(12) United States Patent
Apkarian et al.

(10) Patent No.: US 8,511,945 B2
(45) Date of Patent: Aug. 20, 2013

(54) DRILL ASSEMBLY AND METHOD TO REDUCE DRILL BIT PLUNGE

(75) Inventors: J. G. Agop Apkarian, Toronto (CA); Paul Karam, Toronto (CA); Don Gardner, Burlington (CA)

(73) Assignee: Quanser Consulting Inc., Markham (CA)

( * ) Notice: Subject to any disclaimer, the term of this patent is extended or adjusted under 35 U.S.C. 154(b) by 1116 days.

(21) Appl. No.: 12/413,763

(22) Filed: Mar. 30, 2009

(65) Prior Publication Data
US 2009/0245956 A1    Oct. 1, 2009

Related U.S. Application Data

(60) Provisional application No. 61/040,374, filed on Mar. 28, 2008.

(51) Int. Cl.
*B23B 35/00* (2006.01)
*B23B 45/14* (2006.01)

(52) U.S. Cl.
USPC ............... 408/1 R; 408/7; 408/12; 408/112

(58) Field of Classification Search
USPC ............ 606/80; 408/1 R, 7, 8–13, 14, 16, 408/95, 97, 110, 112
See application file for complete search history.

(56) References Cited

U.S. PATENT DOCUMENTS

| | | | | |
|---|---|---|---|---|
| 3,471,662 A | * | 10/1969 | Berchtold | 200/61.58 R |
| 3,837,757 A | * | 9/1974 | Levine | 408/14 |
| 4,310,269 A | | 1/1982 | Neu et al. | |
| 4,346,444 A | * | 8/1982 | Schneider et al. | 700/173 |
| 4,426,177 A | | 1/1984 | Perry | |
| 4,431,350 A | | 2/1984 | Abrahamson | |
| 4,600,006 A | | 7/1986 | Baker | |
| 4,613,262 A | | 9/1986 | Woods | |
| 4,644,335 A | * | 2/1987 | Wen | 340/683 |
| 4,688,970 A | | 8/1987 | Eckman | |
| 4,699,550 A | | 10/1987 | Baker | |
| 4,723,911 A | * | 2/1988 | Kurtz | 433/27 |
| 4,745,557 A | | 5/1988 | Pekar et al. | |
| 4,803,982 A | | 2/1989 | Baker | |
| 4,830,001 A | | 5/1989 | Walus | |
| 4,854,786 A | * | 8/1989 | Alexander et al. | 408/1 R |

(Continued)

FOREIGN PATENT DOCUMENTS

| | | | |
|---|---|---|---|
| EP | 512867 A2 | * | 11/1992 |
| SU | 859110 A | * | 8/1981 |
| SU | 887073 A | * | 12/1981 |
| WO | WO 2007148114 A1 | * | 12/2007 |

OTHER PUBLICATIONS

International Search Report and Written Opinion of PCT Application No. PCT/CA2009/000411, dated Jun. 29, 2009; Applicant: Quanser Consulting Inc. et al.

*Primary Examiner* — Daniel Howell
(74) *Attorney, Agent, or Firm* — Bereskin & Parr LLP/S.E.N.C.R.L., s.r.l.

(57) ABSTRACT

A drill assembly and method for reducing plunge of a drill bit upon breaking through a workpiece. The drill assembly contains a motor to advance and retract the drill bit, the motor is controlled by a control unit in a feedback loop to achieve a desired stiffness. The control unit determines when the drill bit breaks through the workpiece and stops or retracts the movement of the drill bit.

37 Claims, 6 Drawing Sheets

(56) References Cited

U.S. PATENT DOCUMENTS

| | | | | |
|---|---|---|---|---|
| 4,884,571 | A | 12/1989 | Baker | |
| 4,951,690 | A | 8/1990 | Baker | |
| 5,022,798 | A | 6/1991 | Eckman | |
| 5,073,068 | A * | 12/1991 | Jinkins et al. | 408/17 |
| 5,241,725 | A | 9/1993 | Hamatani et al. | |
| 5,308,198 | A | 5/1994 | Pumphrey | |
| 5,349,337 | A | 9/1994 | McCormick | |
| 5,472,298 | A | 12/1995 | Mihai | |
| 5,876,405 | A | 3/1999 | Del Rio et al. | |
| 6,030,276 | A | 2/2000 | Mortell et al. | |
| 6,033,409 | A | 3/2000 | Allotta | |
| 6,039,514 | A | 3/2000 | O'Donovan et al. | |
| 6,085,121 | A | 7/2000 | Stern | |
| 6,283,684 | B1 | 9/2001 | Jarvis | |
| 6,283,824 | B1 | 9/2001 | Mortell et al. | |
| 6,336,931 | B1 | 1/2002 | Hsu et al. | |
| 6,371,701 | B1 | 4/2002 | Blankenship et al. | |
| 6,517,411 | B2 | 2/2003 | Mortell et al. | |
| 6,565,293 | B2 | 5/2003 | Desmoulins | |
| 6,665,948 | B1 | 12/2003 | Kozin et al. | |
| 6,716,215 | B1 | 4/2004 | David et al. | |
| 6,925,725 | B2 | 8/2005 | Hermann et al. | |
| 7,070,483 | B2 | 7/2006 | Mortell et al. | |
| 7,070,509 | B2 | 7/2006 | Pecastaing | |
| 7,104,997 | B2 | 9/2006 | Lionberger et al. | |
| 7,188,431 | B2 | 3/2007 | Hermann et al. | |
| 7,189,033 | B2 * | 3/2007 | Nappier et al. | 408/1 R |
| 2005/0116673 | A1 * | 6/2005 | Carl et al. | 318/432 |
| 2011/0020084 | A1 * | 1/2011 | Brett et al. | 408/1 R |

* cited by examiner

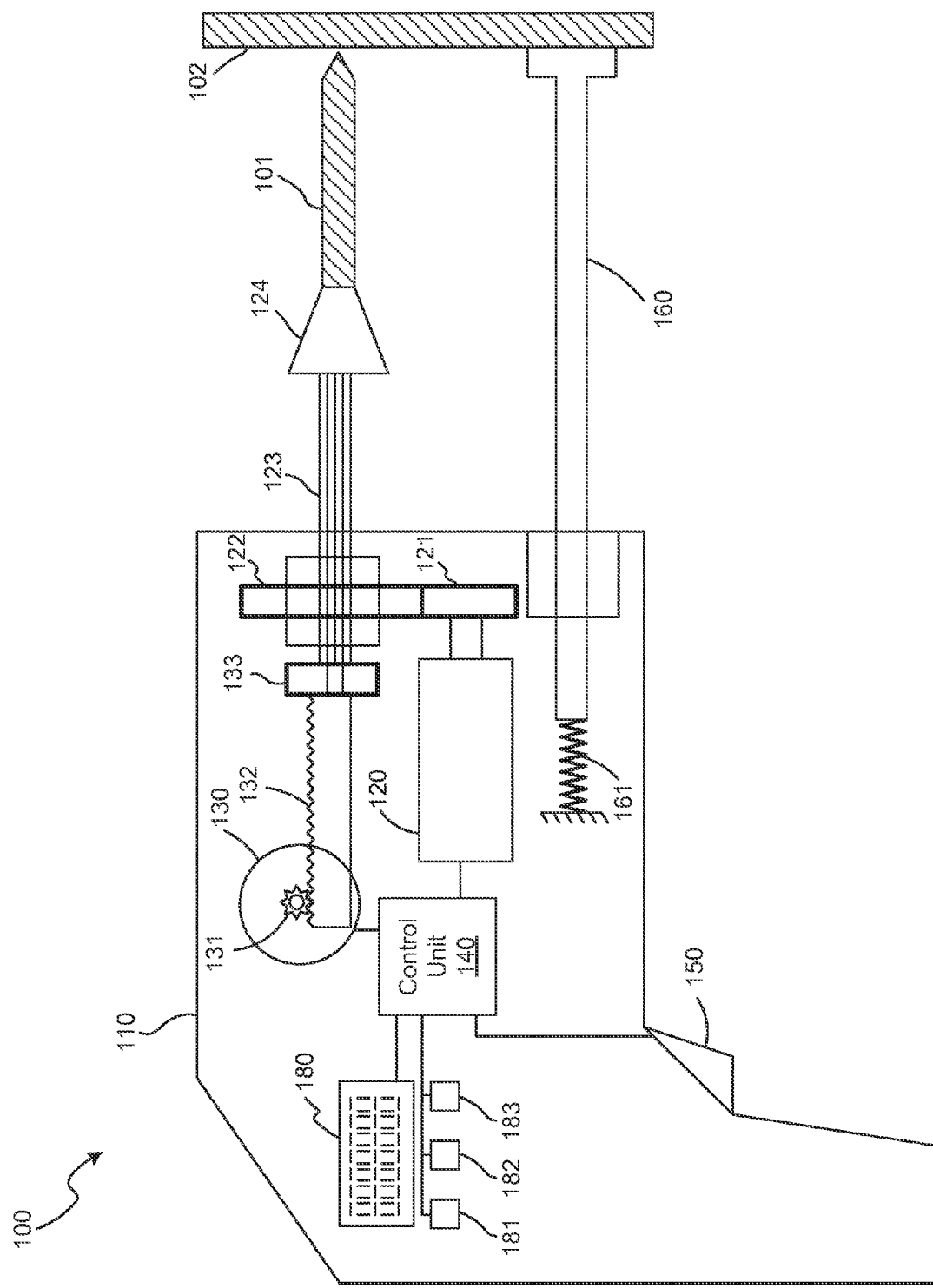

DRILL ASSEMBLY AND METHOD TO REDUCE DRILL BIT PLUNGE

This application claims the benefit of Provisional Application No. 61/040,374, filed Mar. 28, 2008, which is hereby incorporated herein by reference.

FIELD

The present invention relates generally to a drill assembly and method for reducing plunge of the leading edge of a rotating drill bit when the drill bit penetrates a workpiece.

INTRODUCTION

There are many applications where having a drill bit automatically retract after penetrating through a workpiece may be beneficial. For example, in the medical field, a surgical drill that automatically retracts upon penetrating through bone matter may provide greater precision and safety. Manufacturing applications may also benefit from a drill machine with an automatically retracting drill bit through increased speed and efficiency. A power drill incorporating the present invention may also be attractive to the consumer market for providing greater efficiency and safety.

Presently, surgical drills require the surgeon to apply force to the drill towards the bone and to 'feel' the drill bit penetrate through the bone. This process may be time consuming and require considerable skill and experience from the surgeon. Other methods require a costly scan of the area to be drilled to accurately determine the thickness of the bone. Failure to accurately detect penetration through the bone or applying too much force to the drill can result in the drill bit plunging through the bone and damaging sensitive tissue. Other surgical procedures may require a precise hole to be drilled to a certain depth without penetrating the bone.

Present manufacturing techniques may rely on controlling a drill bit to move a certain predetermined distance to penetrate a workpiece. This distance may extend well through the workpiece resulting in a wasted movement of the drill bit. Also, any variance in the thickness of the workpiece would have to be accounted for and may require adjustment or retooling.

SUMMARY

It is therefore an object of the invention to provide a drill assembly and method to reduce plunge of the leading edge of a rotating drill bit when the drill bit penetrates a workpiece.

One aspect of the invention provides for a drill assembly with a drill body, a drill bit rotatably coupled to the drill body, a motor for advancing and retracting the drill bit relative to the drill body, at least one sensor for monitoring the advancement and retraction of the drill bit, and a control unit connected to the motor and at least one sensor, the control unit, on detecting a breakthrough of the drill bit, controlling the motor to reduce plunge of the drill bit.

It is another aspect of the invention to provide a method for reducing plunge of a drill bit through a workpiece by initiating advancement of the drill bit towards the workpiece and detecting the drill bit breaking through the workpiece. It is a further aspect of the invention to maintain a desired stiffness in the forward motion of the drill bit.

In various embodiments, the drill assembly may be a hand held unit or may be adapted to be mounted on an automated or manually operated mechanical assembly such as a robot or mechanical arm.

DRAWINGS

The skilled person in the art will understand that the drawings, described below, are for illustration purposes only. The drawings are not intended to limit the scope of the applicant's teachings in any way.

FIG. 1a is a side functional view of an embodiment of a drill assembly to reduce plunge upon drill bit breakthrough.

DESCRIPTION OF VARIOUS EMBODIMENTS

Figure 1B:
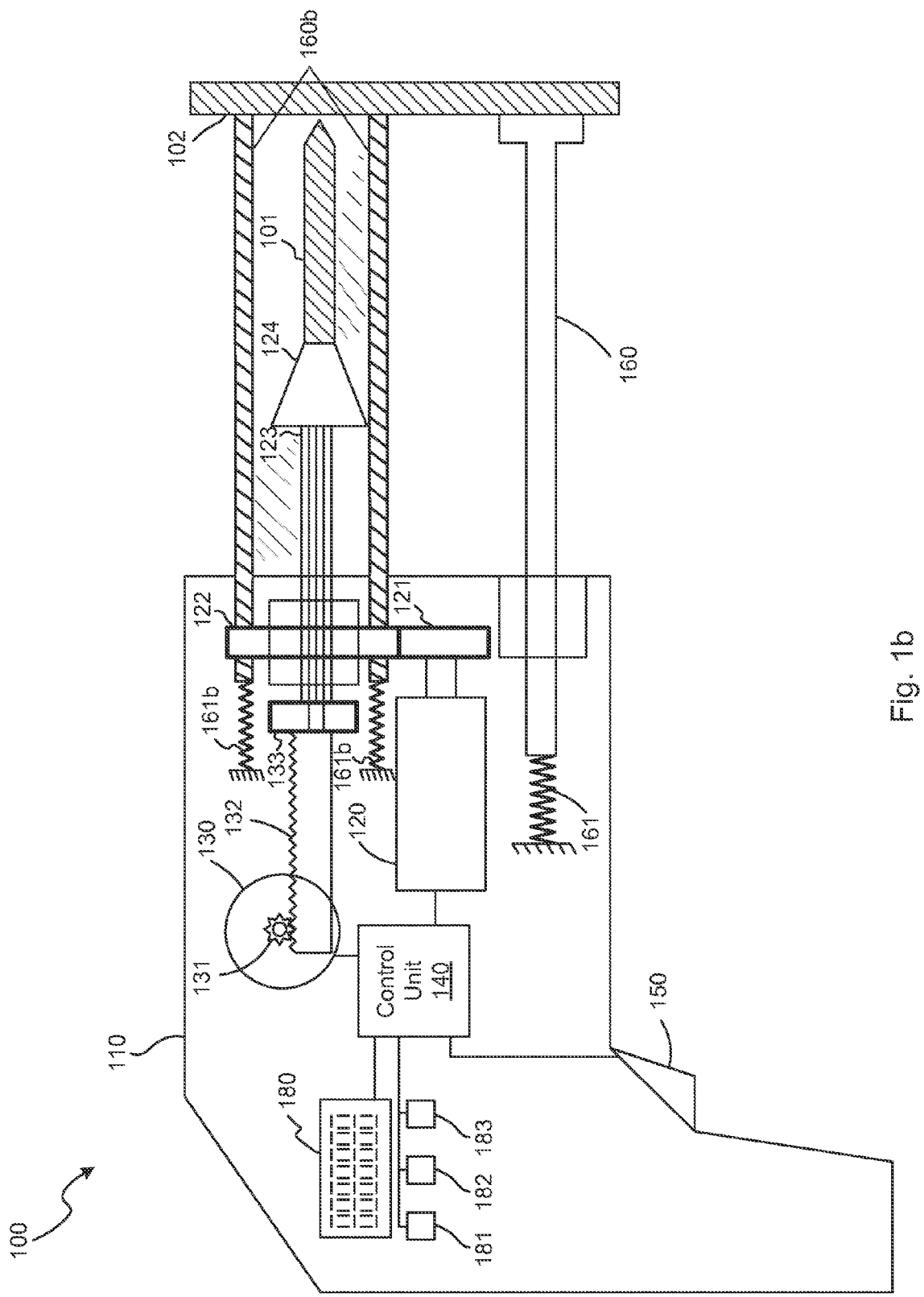
FIG. 1b shows a similar view with the drill bit being surrounded by a stabilizer.

Referring now to FIG. 1a, shown is a side functional view of an embodiment of a drill assembly 100 to reduce plunge upon breakthrough. The drill body 110 provides a casing to enclose the elements of the drill assembly 100. The drill body 110 contains two motors for controlling the motion of the drill bit 101. The workpiece 102, depending on the application, may be any object that requires machining, and may also be human tissue such as bone.

The first motor 130, is responsible for advancing and retracting the drill bit relative to the drill body 110. The motor 130 is attached to drive pinion 131, which in turn is mated to the rack 132 to translate the rotational movement of the motor 130 to a linear motion. Other known mechanisms may be used to generate the advancing and retracting of the drill bit, for example, using a capstan, a lead screw, or a friction drive.

The second motor 120, is responsible for providing the rotational movement for the drill bit 101. The second motor 120 is attached to drive gear 121, which in turn, through gear 122, rotates spindle 123, chuck 124, and drill bit 101 so as to drill through workpiece 102.

Figure 2:
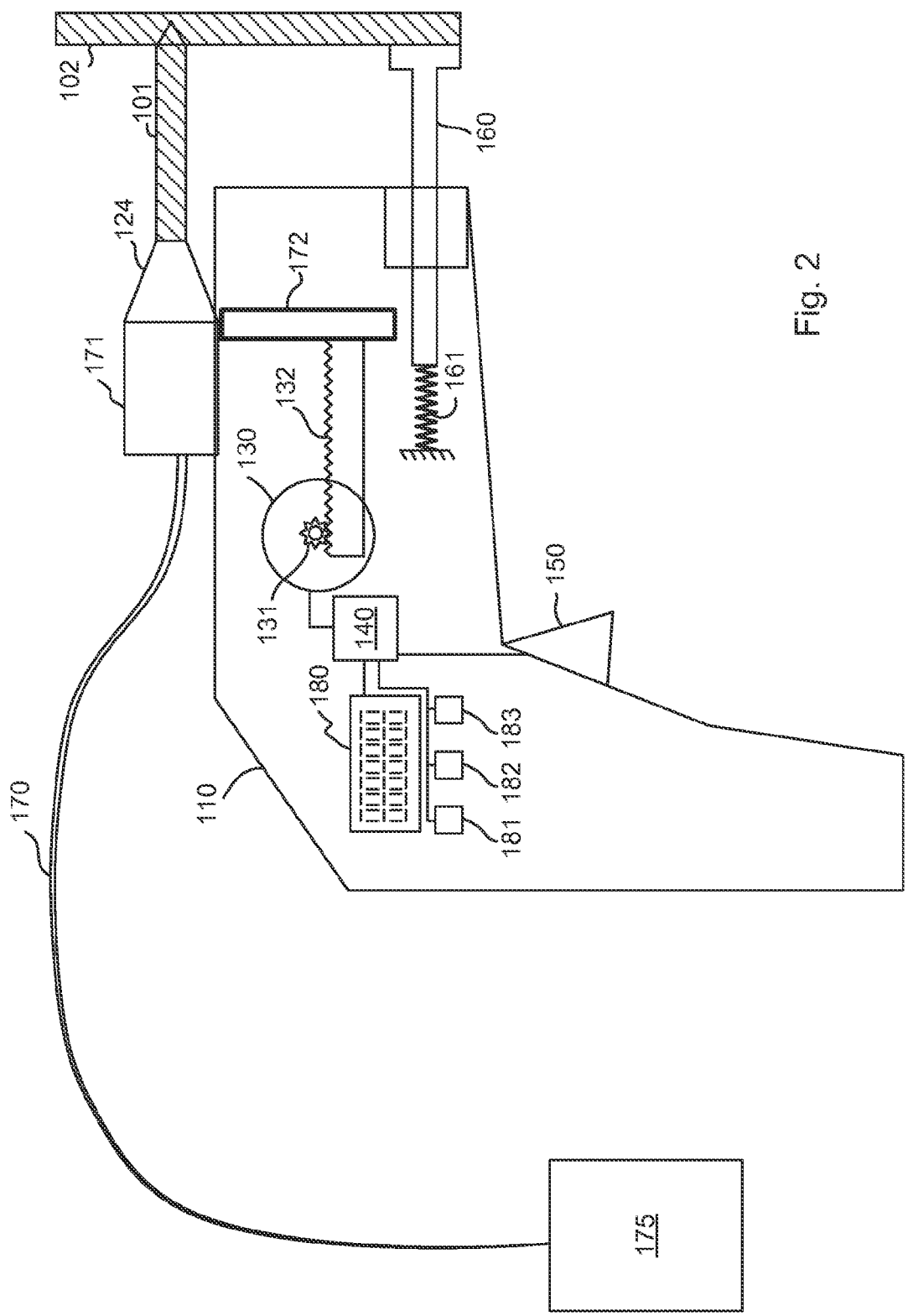
FIG. 2, is a side functional view of an embodiment of a drill assembly connected to an external motor.

In other embodiments, the second motor 120 may be located external to the drill body 110. Referring to FIG. 2, shown is a side functional view of a drill assembly connected to external motor 175. A flexible drive shaft 170 connects external motor 175 to drive housing 171. The drive housing 171 is connected to rack 132 by support 172 to allow the drill bit 101 to be moved towards workpiece 102.

Referring again to FIG. 1a, coupling 133 is connected between rack 132 and spindle 123 to transfer the linear motion of rack 132 to the spindle 123 while allowing spindle 123 to rotate freely.

Control unit 140 is connected to first motor 130 and second motor 120. Control unit 140 may be, for example, a microprocessor capable of processing a number of analog and digital signals, and providing a number of analog and digital outputs to control connected devices. The control unit 140 is configured to control motors 120 and 130 and receive feedback from motors 120 and 130. The control unit 140 processes the feedback in order to appropriately control motors 120 and 130.

Such feedback may include signals from one or a number of sensors, including, position sensors to measure the position of the drill bit, accelerometers, current or power measurement, and torque sensors. The control unit 140 may also monitor such sensors to perform control operation based on a detected rate of change from the sensors. Through this feedback loop the motor 130 is controlled to maintain a fixed stiffness of the drill bit 101 against the workpiece 102. This stiffness affects the amount of force that can be applied to the workpiece 102 by the drill bit 101. The desired stiffness is programmable and may vary depending on the application.

While the control unit 140 shown in FIG. 1 is within the drill body 110, it can be appreciated that in some applications the control unit 140 could be located outside of the drill body 110. For example, but not limited to, in a CNC drill machine there may be a general purpose computer or microprocessor connected to the machine that acts as the control unit 140.

Stabilizer 160 is attached to the drill body and acts to support the drill body on the workpiece 102 and maintain spacing between the drill body 110 and the workpiece 102. If the workpiece is curved, stabilizer 160 may also help in aligning drill body 110 so that drill bit 101 is perpendicular with the workpiece. The stabilizer 160 may be attached to biasing means 161. In some embodiments, the biasing means may be spring loaded. In other embodiments, the biasing means may be damping loaded, for example, by using a gas spring damper, such as that supplied by H. A. Guden Co., Inc. of Ronkonkoma, N.Y.

In some embodiments, stabilizer 160 may be positioned close to the drill bit 101 to support the drill body 110 upon a curved workpiece. Referring briefly to FIG. 1*b*, in some embodiments the stabilizer may be a hollow cylinder 160*b* surrounding the drill bit 101, where the stabilizer is made up of a transparent material to allow the user of the drill to observe the drill bit 101 at the workpiece 102. The stabilizer 160*b* may be attached to biasing means 161*b*. For example, but not limited to, a surgical drill for cranial drilling may have a hollow cylindrical stabilizer surrounding the drill bit made of transparent plastic. The stabilizer may also be detachable to allow for sterilization or replacement.

Upon powering on the drill assembly, control unit 140 will initialize and calibrate sensors. The control unit 140 will initialize the drill bit position into a retracted position.

Trigger 150 is connected to the control unit 140 to allow users of the drill assembly to control the operation of the drill assembly 100. In some embodiments trigger 150 may be a start/stop switch that is used to start and stop the drill operation. When a user depresses the trigger, the control unit will initiate the rotation and advancement of the drill bit 101. The rate of rotation and rate of advancement may be predetermined according to the application. For example, if the application of the drill assembly 100 is solely for use in drilling a certain material, the control unit may be configured to use a specific rate of rotation and rate of advancement for that application. In other embodiments, the drill assembly 100 may have a mode switch to select the application or the properties of the workpiece 102 in order to configure the control unit to select an appropriate rate of rotation and rate of advancement of the drill bit 101.

In other embodiments, the trigger 150, rather than a start/stop switch, may be variable or pressure sensitive to allow a user of the drill assembly 100 more precise control. For example, but not limited to, the control unit 140 may interpret the state of trigger 150 to correspond to a user selected rate of rotation of the drill bit 101, or to a user selected rate of advancement of the drill bit towards the workpiece 102. The control unit 140 can regulate the motors 120 and 130 to maintain either a user controlled, through use of trigger 150, constant rate of rotation or constant rate of advancement.

The control unit 140 may monitor a signal or combination of signals to determine whether the drill bit 101 has made contact with or broken through the workpiece 102. As the drill bit 101 makes contact with the workpiece 102, there will be increased resistance to the rotation and advancement of the drill bit 101. Similarly, as the drill bit 101 breaks through the workpiece 102 there will be decreased resistance to the rotation and advancement of the drill bit 101. Also, in cases where the workpiece is made up of a number of layers, each layer may provide a different resistance to the rotation and advancement of the drill bit 101. The control unit 140 may monitor this change of resistance in a number of ways.

In some embodiments, the control unit 140 may be configured to detect a change in speed of the advancing motion of the drill bit 101. The control unit 140 may monitor one or a number of sensors to detect that the drill bit 101 has made contact with or broken through the workpiece 102. Such sensors may include, position sensors to measure the position of the drill bit, accelerometers, current or power measurement, and torque sensors for the motors. The control unit 140 may also monitor such sensors to perform control operation based on a detected rate of change from the sensors.

In some embodiments, the control unit 140 may be configured to detect a change in torque from either of the motors 120 or 130. The change of resistance to the drill bit 101 upon contact or breakthrough will result in a corresponding changing in torque applied by motors 120 and 130. In other embodiments, the power or current delivered to the motors 120 and 130 may be monitored by the control unit 140 to determine a change in torque applied by the motors.

In other embodiments, the drill assembly may contain a microphone directed towards the drill bit to detect breakthrough. Control unit 140 is connected to the microphone and monitors the received signal. The act of the drill bit 101 drilling through the workpiece 102 will result in a sound. A change in resistance to the rotation of the drill bit 101 will result in a change pitch or frequency of this sound. The control unit 140 will detect a change in pitch or frequency in the received signal to determine if the drill bit 101 has made contact with or broken through the workpiece 102.

Control unit 140, upon detecting breakthrough, can control the operation of the drill in order to reduce the plunge of the drill bit 101 through the workpiece 102. In some embodiments, control unit 140, upon detecting breakthrough, will stop the advancement of the drill bit 101 by stopping first motor 130. The motor may stop the rotation of drive pinion 131 to hold the drill bit 101 in a fixed position relative to the drill body 110, or the motor may allow drive pinion 131 to spin freely thereby allowing the drill bit 101 to move freely relative to the drill body 110. Other embodiments could stop the advancement of the drill bit 101 by employing a clutch mechanism attached to drive pinion 131 that can be controlled by the control unit 140 to disengage the drive pinion 131 from the motor 130. The use of a clutch mechanism could also allow the drive pinion 131 to spin freely so that pushing the drill body 110 towards the workpiece 102 would cause the drill bit 101 to move into the drill body 110.

In other embodiments of the invention, the drill bit 101 may be controlled to retract the drill bit upon detecting breakthrough in order to reduce plunge of the drill bit 101 through workpiece 102. The control unit 140, upon detecting breakthrough, will reverse the advancement of the drill bit 101 by reversing motor 130.

Some embodiments of the invention may incorporate an indicator to alert the user of the drill that breakthrough has occurred. For example, but not limited to, the drill may include a light emitting diode controlled by the control unit 140 that glows red once drill bit 101 has penetrated workpiece 102. Alternatively, the drill may include a speaker, controlled by the control unit 140, that emits an audible tone to indicate that drill bit 101 has penetrated workpiece 102.

In other embodiments, the stopping or reversing of the advancement of the drill bit may be combined with controlling the rotation of the drill bit upon detecting breakthrough. For example, but not limited to, the control unit 140 may stop the rotation of the drill bit 101 by stopping the motor 120 or disengaging the drive mechanism of the spindle 123. Alternatively, the control unit 140 can reverse the rotation of the drill bit 101 by reversing the motor 120. Reversing the rotation of the drill bit 101 may assist in removing drill bit 101 from workpiece 102.

Figure 3:
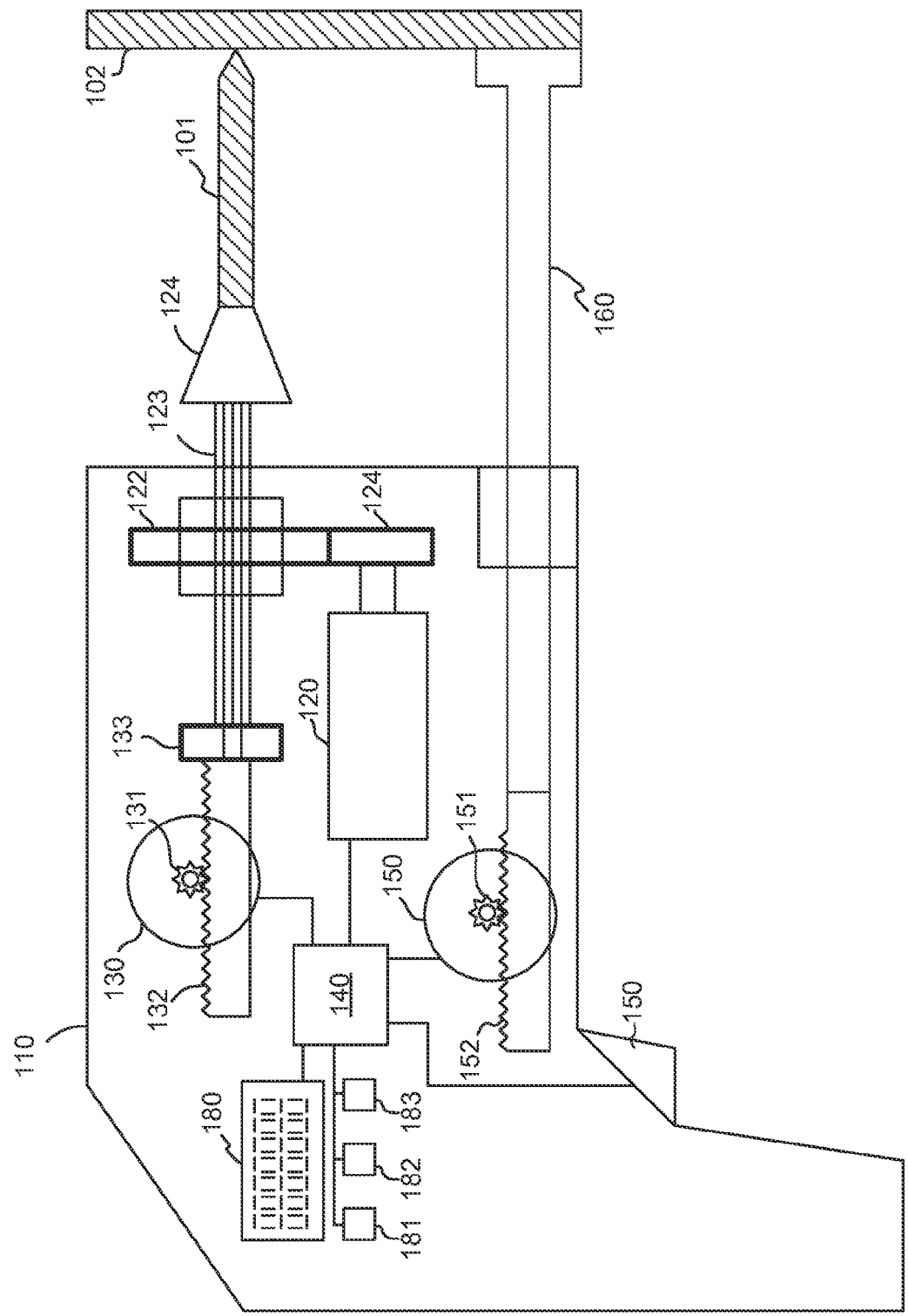
FIG. 3 is a side function view of an embodiment of a drill assembly with an attached actuated stabilizer.

Now referring to FIG. 3, shown is a side functional view of a drill assembly with an actuated stabilizer attached to the drill body. Stabilizer 160 is connected to rack 152 that may be advanced or retracted by the drive pinion 151 connected to the stabilizer motor 150. The stabilizer motor 150 is controlled and monitored by the control unit 140. The control unit 140 will monitor feedback from the stabilizer motor 150 to determine if there is a change in resistance of the advancement of the drill body 110 towards the workpiece 102. As an alternate or complementary method of removing the drill bit 101 from workpiece 102 upon detecting breakthough, control unit 140 may control motor 150 to cause stabilizer 160 to extend and push the drill body 110 away from the workpiece 102, or alternatively, to stop the motor to stiffen the stabilizer 160.

The stabilizer can be controlled to achieve a desired stiffness similar to the servo loop control applied to motor 130, as described above.

In other embodiments, the control unit 140 may monitor feedback from motor 130 to determine the distance that the drill bit 101 has penetrated the workpiece 102. Through monitoring the change in resistance as described above, the control unit 140 can measure depth that drill bit 101 has traveled between making contact with the workpiece 102 until breakthrough.

Referring to FIG. 1a, the control unit 140 may interface with display 180 that would show the distance that the drill bit 101 has drilled through workpiece 102. In other embodiments, the drill assembly may provide for buttons 181, 182, and 183 in conjunction with display 180 to allow a user to select a desired drilling depth. The control unit 140 would then automatically retract drill bit 101 when the selected drilling depth was reached. Alternatively, the control unit 140 could be configured to automatically retract drill bit 101 at earliest of reaching the selected depth or the detection of breakthrough, so as to allow the user to select an upper limit or safety limit for drill bit depth.

In some embodiments of the present invention the drill assembly may provide a button to allow a user to control the operation of the drill by selecting the properties of workpiece 102. For example, in a workpiece having multiple layers, each layer having a different resistance to drill bit 101, the user may select the properties of the workpiece 102 so that the drill bit 101 will continue to drill through a subsequent layer even if it provides less resistance to drill bit 101. In a surgical drill this may allow a surgeon drill through a bone containing marrow. Rather than the drill retracting after it penetrates the first layer of bone, the drill bit will continue through the marrow and only retract after it has penetrated the second layer of bone. Other applications may allow for the drill bit to stop and retract when it reaches a certain layer of the material.

Figure 4:
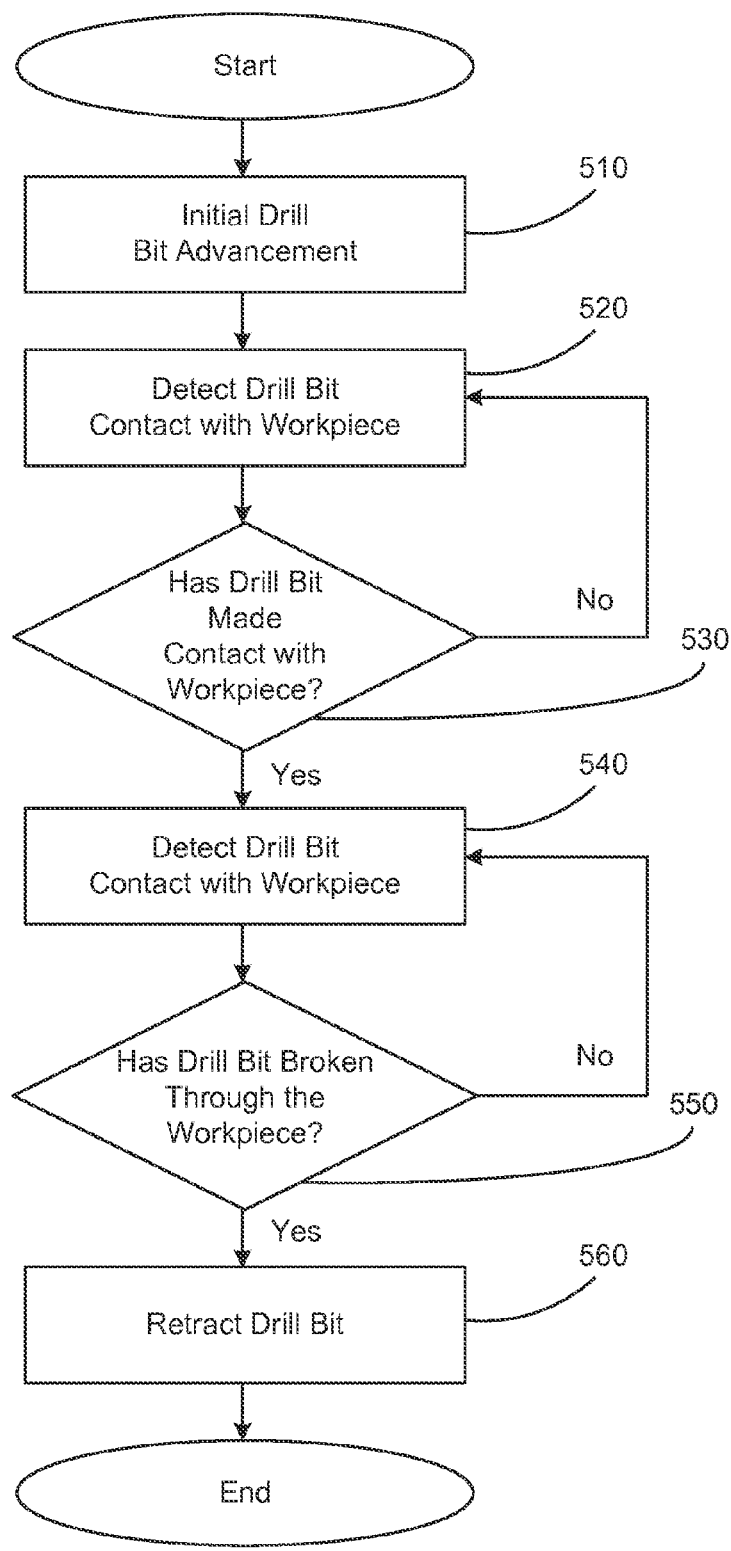
FIG. 4 is a block diagram of a method for reducing drill bit plunge upon breakthrough.

Now referring to FIG. 4, shown is a block diagram of a method for reducing the plunge of the drill bit upon breaking through the workpiece. At step 510, the advancement of drill bit 101 is initiated. In embodiments where drill 100 is directly controlled by a user, step 510 may be initiated by the user pressing the trigger 150. Alternatively, in a computer controlled embodiment, a software program running on control unit 140 or an external computer system interfacing with the control unit 140.

In step 520, control unit 140 monitors whether drill bit 101 has made contact with workpiece 102. As described above, control unit 140 monitors for an increase in resistance to the rotation and advancement of the drill bit 101. In step 530, control unit 140 continues to monitor whether drill bit 101 has made contact with workpiece 102, and if so, continues to step 540.

In step 540, control unit 140 monitors whether drill bit 101 has broken through the workpiece 102. As described above, control unit 140 monitors for a decrease in resistance to the rotation and advancement of the drill bit 101. In step 550, control unit 140 continues to monitor whether drill bit 101 has broken through workpiece 102, and if so, continues to step 560. In step 560, drill bit 101 is retracted from workpiece 102 towards the drill body to reduce the plunge through of drill bit 101. Optionally, the rotation of drill bit 101 may also be stopped in step 560 before, while or after the drill bit is retracted from the workpiece 102.

Figure 5:
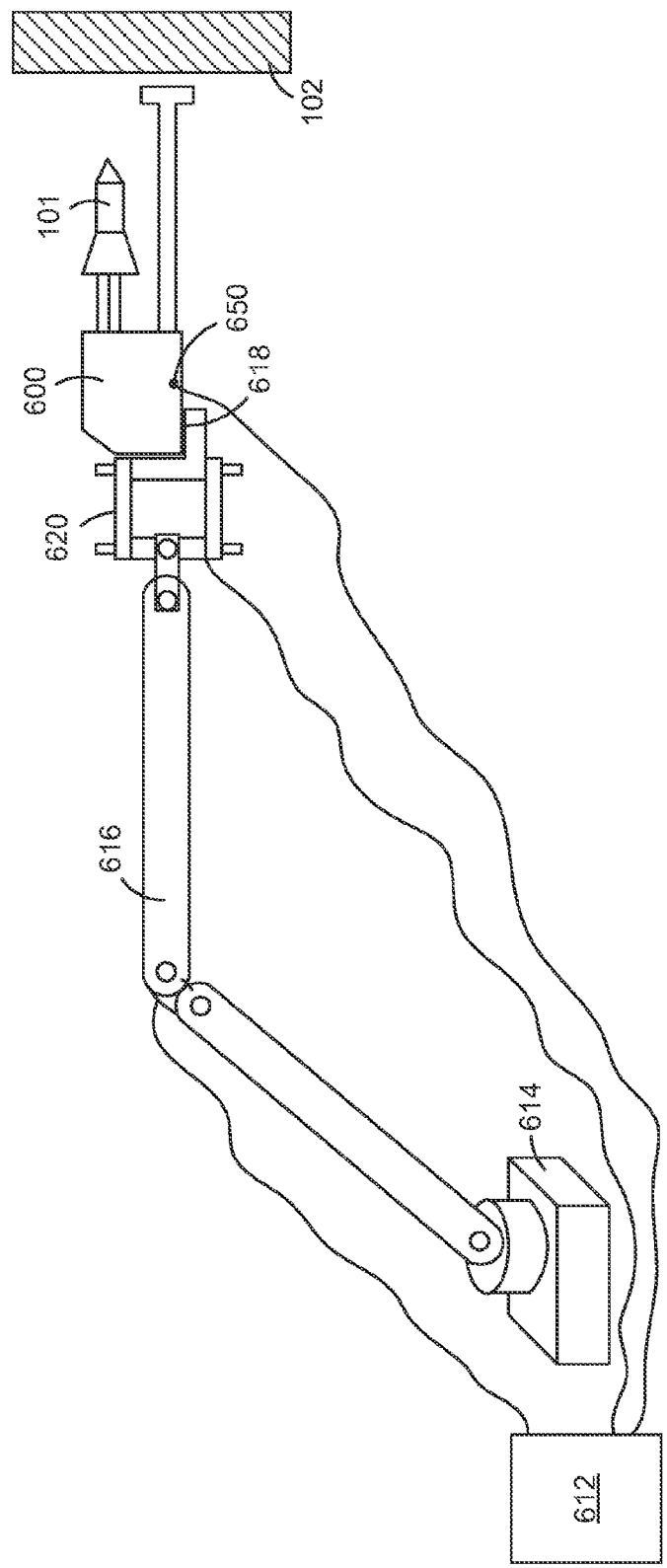
FIG. 5 illustrates a drill assembly mounted on a mechanical arm.

Reference is next made to FIG. 5, which illustrates a drill assembly 600 mounted a robot 610. Robot 610 has a control system 612, a base 614, an articulated arm 616 and a mounting bracket 618. Mounting bracket 618 is coupled to arm 616 through a three-degree of freedom joint linkage 620. In other embodiments, the mounting bracket 618 may be fixedly mounted to arm 616 or may be mounted with a linkage that provides any number of degrees of freedom. Drill assembly 600 is similar to drill assembly 100 in its design and operation, but is adapted for use with robot 610. Drill assembly 600 is mounted to mounting bracket 618 to hold drill assembly 600 fixedly to mounting bracket 618. Drill assembly also has a speed control input 650 that replaces the trigger 150 of drill assembly 100. Speed control input 650 is coupled is to the control system 612 to receive speed control information. The speed control information is provided to the control unit 140 (FIG. 1a) which regulates motors 120 and 130 (FIG. 1a) in response to the speed control information. Control system 612 also receives signals from control unit 140, including an "operation complete" signal.

Control system 612 may be configured by a user to drill a desired hole or carry out some other operation in a specified position. Control system 612 is coupled to arm 616 (or more precisely to the joints of arm 616) and linkage 620 to position drill assembly 600 in to drill the desired hole in workpiece 102. Control system 612 then activates drill assembly 600 by transmitting speed control information and advances it axially to drill the desired hole. The hole is drilled according to method of FIG. 4. When the drill bit is retracted, the control unit 140 transmits an operation complete signal to the control system 612. Control system 612 then sets the speed control information transmitted to control system 140 to request no rotation of the drill bit 101 (the rotation of the drill bit may optionally already be stopped as part of step 560). Control system 612 also retracts the drill assembly to extract it from workpiece 102.

In other embodiments, drill assembly 100 may be mounted on a manually operated mechanical base. For example, the mechanical base may allow drill assembly to be positioned to drill a desired hole and then allow the drill assembly to moved axially to drill the hole. In other embodiments, drill assembly 600 may be mounted in an automated mechanical base different in design and operation from robot 610, but which also controls the movement and operation of the drill assembly 600. In other embodiments, the robot 610 may be adapted to allow a user to manually position drill assembly 600, and then automatically operate drill assembly 600 by automatically advancing the drill assembly and by transmitting speed control instructions.

Those skilled in the art will appreciate that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. A drill assembly comprising:
   a drill body;
   a drill bit rotatably coupled to the drill body;
   a motor for advancing and retracting the drill bit relative to the drill body;
   at least one sensor for monitoring the advancement and retraction of the drill bit; and
   a control unit connected to the motor and at least one sensor, the control unit being configured to measure a change in speed of advancing motion of the drill bit relative to the drill body to detect breakthrough of a workpiece and, on detecting a breakthrough, control the motor to reduce plunge of the drill bit.

2. The drill assembly of claim 1, wherein the control unit monitors the at least one sensor to maintain a desired stiffness of the drill bit.

3. The drill assembly of claim 1, further comprising a support attached to the drill body.

4. The drill assembly of claim 3, wherein the support is a stabilizer extending from drill body to a workpiece to resiliently support the drill body.

5. The drill assembly of claim 4, wherein the control unit is configured to measure an increase in speed of the advancing motion of the stabilizer to detect breakthrough.

6. The drill assembly of claim 1, wherein the control unit is configured to measure an increase in speed of the advancing motion of the drill bit relative to the drill body to detect breakthrough.

7. The drill assembly of claim 1 wherein the at least one sensor is a microphone connected to the control unit, wherein the control unit is configured to measure a change in pitch from the microphone to detect breakthrough.

8. The drill assembly of claim 1 further comprising a second motor for rotating the drill bit, wherein the control unit is configured to measure a change in torque of the second motor to detect breakthrough.

9. The drill assembly of claim 8, wherein the control unit is configured to measure a reduction in power used by the second motor to detect breakthrough.

10. The drill assembly of claim 8, wherein the control unit is configured to control the second motor to maintain a constant rate of rotation of the drill bit.

11. The drill assembly of claim 8, wherein the control unit is configured to control the second motor to stop the rotation of the drill bit upon retraction.

12. The drill assembly of claim 8, wherein the control unit is configured to control the second motor to reverse the rotation of the drill bit upon retraction.

13. The drill assembly of claim 8 further comprising a variable trigger connected to the control unit to control the second motor to maintain a constant rate of rotation of the drill bit as selected by the variable trigger.

14. The drill assembly of claim 8, wherein the motors are selected from the group of pneumatic motors and electric motors.

15. The drill assembly of claim 3, wherein the stabilizer is spring loaded.

16. The drill assembly of claim 3, wherein the stabilizer is damping loaded.

17. The drill assembly of claim 4, wherein the stabilizer surrounds the drill bit.

18. The drill assembly of claim 4, wherein the stabilizer is transparent.

19. The drill assembly of claim 3, wherein the control unit is configured to stiffen the stabilizer upon breakthrough.

20. The drill assembly of claim 3, wherein the control unit is configured to actuate the stabilizer to move the drill body away from the workpiece upon breakthrough.

21. The drill assembly of claim 3, wherein the control unit monitors the at least one sensor to maintain a desired stiffness of the stabilizer.

22. The drill assembly of claim 1, wherein the control unit is configured to measure a displacement of the drill bit after the drill bit has made contact with the workpiece.

23. The drill assembly of claim 22, wherein the control unit is configured to retract the drill bit upon the displacement of the drill bit reaching a threshold.

24. The drill assembly of claim 1, wherein the control unit is configured for multilayer drilling.

25. The drill assembly of claim 1 further comprising an indicator to identify breakthrough.

26. The drill assembly of claim 23, wherein the indicator is a speaker connected to the control unit.

27. The drill assembly of claim 23, wherein the indicator is a light emitting device connected to the control unit.

28. A method for reducing plunge of a drill bit through a workpiece, the method comprising:
    initiating advancement of the drill bit towards the workpiece; and
    detecting the drill bit breaking through the workpiece by measuring a change in speed of advancing motion of the drill bit relative to a drill body.

29. The method of claim 28 further comprising maintaining a desired stiffness of the drill bit.

30. The method of claim 29 further comprising retracting the drill bit on detecting the drill bit breaking through the workpiece.

31. The method of claim 29 further comprising stopping the advancement of the drill bit on detecting the drill bit breaking through the workpiece.

32. The method of claim 28, wherein detecting comprises measuring an increase in rate of advancement of the drill bit towards the workpiece.

33. The method of claim 28, wherein detecting comprises measuring a change in audible pitch from the drill bit.

34. The method of claim 28, wherein detecting comprises measuring a change in torque of a motor for rotating the drill bit.

35. The method of claim 30, wherein retracting the drill bit further comprises stopping rotation of the drill bit.

36. The method of claim 30, wherein retracting the drill bit further comprises reversing rotation of the drill bit.

37. A method for measuring penetration depth of a drill bit through a workpiece, the method comprising:
    initiating advancement of the drill bit towards the workpiece;
    detecting contact of the drill bit with the workpiece to begin measuring drill bit penetration;
    detecting the drill bit breaking through the workpiece to end measuring drill bit penetration, where the drill breaking through the workpiece is detected by measuring a change in speed of advancing motion of the drill bit relative to a drill body; and outputting penetration measurement to a display.

* * * * *